US00PP12633P2

(12) United States Plant Patent
Meerow

(10) Patent No.: US PP12,633 P2
(45) Date of Patent: May 21, 2002

(54) AMARYLLIS PLANT NAMED 'RIO'

(75) Inventor: Alan Meerow, Davie, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 09/396,481

(22) Filed: Sep. 15, 1999

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Wendy A. Baker
(74) *Attorney, Agent, or Firm*—C. A. Whealy

(57) ABSTRACT

A distinct cultivar of Amaryllis plant named 'Rio', characterized by its red purple petals and sepals with median silvery pink keels; intense fragrance; resistance to Red Scorch Fungus; and excellent high temperature tolerance.

1 Drawing Sheet

BACKGROUND OF THE INVENTION

The present invention relates to a new and distinct cultivar of Amaryllis plant, botanically known as Hippeastrum hybrid and referred to by the cultivar name Rio.

The new cultivar is a product of a planned breeding program conducted by the Inventor in Fort Lauderdale, Fla. The objective of the breeding program is to develop new Amaryllis cultivars with novel flower coloration patterns and fragrance.

The new Amaryllis originated from a cross made by the Inventor in Fort Lauderdale, Fla., of an unidentified proprietary selection of the interspecific cross *Hippeastrum papilio*×*Hippeastrum ambiguum* 'Tweedianum' (not patented), as the female, or seed, parent with the Hippeastrum hybrid cultivar Dutch Belle (not patented), as the male, or pollen, parent.

The cultivar Rio was discovered and selected by the Inventor as a flowering plant within the progeny of the stated cross in a controlled environment in Fort Lauderdale, Fla., in 1994. The selection of this new Amaryllis plant was based on its unique flower coloration pattern.

Plants of the new Amaryllis differ from plants of the female parent in the following characteristics:

1. Plants of the new Amaryllis have red purple petals and sepals with median silvery pink keels whereas plants of the female parent have red on a green background petals and sepals.
2. Flowers of plants of the new Amaryllis are much larger with broader petals and sepals than flowers of plants of the female parent.
3. Plants of the new Amaryllis have shorter scapes than plants of the female parent.

Plants of the new Amaryllis differ from plants of the male parent in the following characteristics:

1. Plants of the new Amaryllis have red purple petals and sepals with median silvery pink keels whereas plants of the male parent have solid red purple petals and sepals.
2. Flowers of plants of the new Amaryllis are intensely fragrant whereas flowers of plants of the male parent are only mildly fragrant.
3. Plants of the new Amaryllis have shorter and darker green leaves than plants of the male parent.

4. Plants of the new Amaryllis are more resistant to Red Scorch Fungus (*Staganospora curtisii*) than plants of the male parent.
5. Plants of the new Amaryllis are more high temperature tolerant than plants of the male parent.

Asexual reproduction of the new cultivar by twin-scale cuttings taken in a controlled environment in Fort Lauderdale, Fla., has shown that the unique features of this new Amaryllis are stabel and reproduced true to type in successive generations.

SUMMARY OF THE INVENTION

The cultivar Rio has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Rio'. These characteristics in combination distinguish 'Rio' as a new and distinct cultivar:

1. Flowers of plants of the new Amaryllis have red purple petals and sepals with median silvery pink keels.
2. Flowers of plants of the new Amaryllis are intensely fragrant.
3. Plants of the new Amaryllis are resistant to Red Scorch Fungus, *Staganospora curtisii.*
4. Plants of the new Amaryllis have exhibited excellent high temperature tolerance.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a close-up view of typical flowers of 'Rio'. Flower colors in the photograph may appear different from the actual colors due to light reflectance.

DETAILED BOTANICAL DESCRIPTION

The following observations, measurements and values describe plants of the new cultivar that were about two years old from a bulb scale cutting and grown in Fort Lauderdale, Fla., in a polypropylene-covered shadehouse that provided a 50% reduction in ambient light. During the flowering period, day temperatures ranged from 25 to 30° C. and night temperatures ranged from 15 to 18° C.

Color references are made to The Royal Horticultural Society Colour Chart except where general terms of ordinary dictionary significance are used.

Botanical classification: Hippeastrum hybrid cultivar Rio.

Parentage:

*Female or seed parent.*—Unidentified proprietary selection of *Hippeastrum papilio*×*Hippeastrum ambiguum* 'Tweedianum', not patented.

*Male or pollen parent.*—Hippeastrum hybrid cultivar Dutch Belle, not patented.

Propagation:

*Type.*—Twin-scale cuttings.

*Time to initiate roots, summer.*—About 30 days at temperatures of 30° C.

*Time to develop roots, winter.*—About 40 days at temperatures of 22° C.

*Time to develop roots, summer.*—About 65 days at temperatures of 30° C.

*Time to initiate roots, winter.*—About 90 days at temperatures of 22°C.

*Rooting description.*—White; numerous; fine and fibrous to moderately thick and fleshy; freely branching.

Plant description:

*Appearance.*—Perennial herbaceous Amaryllis. Upright and clumping growth habit.

*Crop time.*—From bulb scale cuttings, about two years are required to produce a finished, flowering plant in a 15 to 20-cm container.

*Vigor.*—Moderately vigorous.

*Plant height.*—About 51 cm.

*Plant spread.*—About 50 cm.

*Foliage description.*—Arrangement: Distichous, single. Quantity: About 5 per plant. Length, mature leaves: About 28.5 cm. Width, mature leaves: About 6 cm. Shape: Lorate. Apex: Acute. Margin: Entire. Texture: Coarse; glabrous. Color: Young foliage, upper surface: 144A. Young foliage, lower surface: 144B. Mature foliage, upper surface: 137B. Mature foliage, lower surface: 137D.

Flower description:

*Appearance.*—Broad funnel-shaped single flowers arranged in umbels. Corolla and calyx three-parted and fused at the base. Freely flowering, typically about four open flowers per scape and about 10 flowers and flower buds per plant. Flowers last about three or four days. Flowers persistent. Flowers held horizontally, perpendicular to scape.

*Flowering response.*—Plants flower in the spring. Plants typically flower about March 1 to March 21 in Fort Lauderdale, Fla.

*Fragrance.*—Intense.

*Flower diameter.*—About 18 cm.

*Flower depth* (*height*).—About 13 cm.

*Flower buds.*—Length: About 4 cm. Width: About 1 cm. Shape: Oblanceolate. Color: 66B. Rate of flower bud opening: About 1 to 2 days.

*Petals.*—Length: About 13.5 cm. Width: About 5.5 cm. Shape: Broadly elliptic. Apex: Apiculate. Margin: Entire. Texture: Smooth; waxy. Color: When opening, upper surface: Red purple, 66B. When opening, lower surface: Red purple, 66B. Fully opened, upper surface: Red purple, 66B, with silvery pink, 65D to 75C, keels; main color fading to 66D with subsequent development. Fully opened, lower surface: Red purple, 66B.

*Sepals.*—Shape: Elliptic. Apex: Apiculate. Margin: Entire. Color: Upper surface: Red purple, 66B, with silvery pink, 65D, keels; main color fading to 66D with subsequent development. Lower surface: Red purple, 66B.

*Scape.*—Length: About 51 cm. Diameter: About 2 cm. Appearance/aspect: Leafless; upright; not fasciated. Strength: Strong. Texture: Smooth. Color: 137D.

*Reproductive organs.*—Androecium: Stamen number: Six. Anther shape: Elliptic. Anther size: About 3 to 4 mm. Anther color: White. Pollen amount: Moderate. Pollen color: Yellow. Gynoecium: Pistil number: One. Pistil length: About 16 cm. Stigma shape: Trifid. Stigma color: 66D. Style length: About 16 cm. Style color: 66B. Ovary color: 141C.

*Seed.*—Seed development has not been observed.

Bulb description:

*Diameter.*—About 7.3 cm.

*Circumference.*—About 24 cm.

*Shape.*—Ovoid.

*Color.*—149A; tunic, 165A.

*Offsets produced per year.*—About two or three offsets per bulb.

Disease resistance: Plants of the new Amaryllis have been shown to be resistant to Red Scorch Fungus, *Staganospora curtisii.*

Heat tolerance: Plants of the new Amaryllis have demonstrated good tolerance to high temperatures about 33 to 35° C.

It is claimed:

1. A new and distinct cultivar of Amaryllis plant named 'Rio', as illustrated and described.

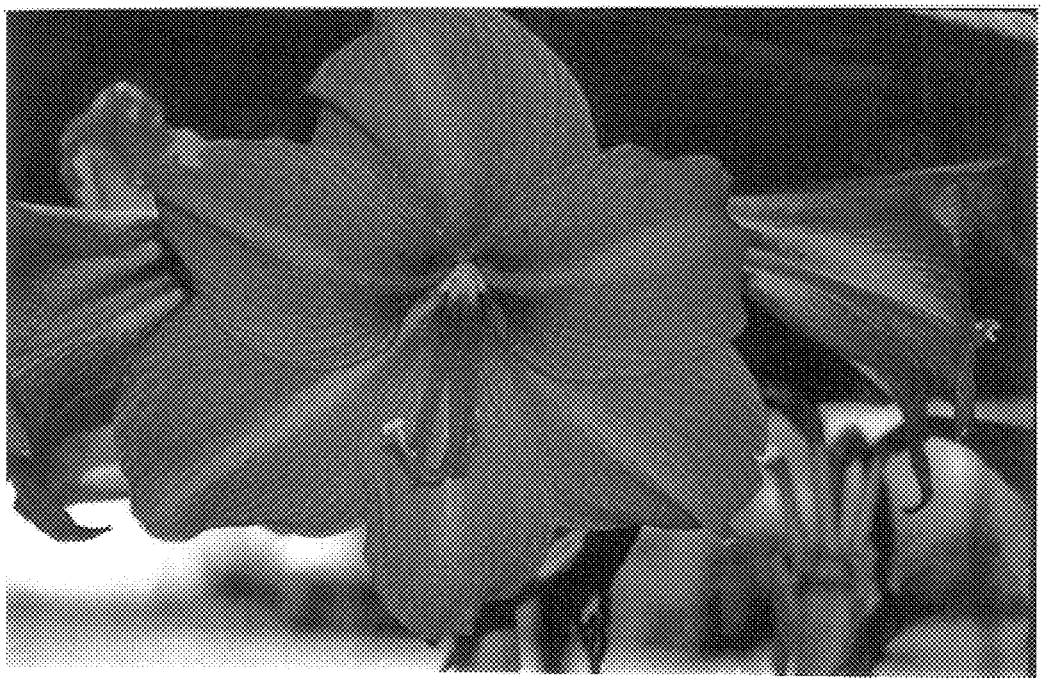

* * * * *